(12) United States Patent
Griffiths et al.

(10) Patent No.: US 7,887,587 B2
(45) Date of Patent: Feb. 15, 2011

(54) SOFT TISSUE SPACER

(75) Inventors: Bryan Griffiths, Coatesville, PA (US); Ross J. Hamel, West Chester, PA (US)

(73) Assignee: Synthes USA, LLC, West Chester, PA (US)

( * ) Notice: Subject to any disclaimer, the term of this patent is extended or adjusted under 35 U.S.C. 154(b) by 854 days.

(21) Appl. No.: 10/860,885

(22) Filed: Jun. 4, 2004

(65) Prior Publication Data

US 2005/0273165 A1 Dec. 8, 2005

(51) Int. Cl.
*A61F 2/28* (2006.01)
(52) U.S. Cl. .................................... 623/16.11
(58) Field of Classification Search .............. 623/11.11, 623/16.11, 23.5, 23.51, 23.53, 23.55, 23.57, 623/23.58, 23.6
See application file for complete search history.

(56) References Cited

U.S. PATENT DOCUMENTS

| | | | |
|---|---|---|---|
| 3,178,728 A | 4/1965 | Christensen | |
| 3,488,779 A | 1/1970 | Christensen | |
| 3,579,643 A | 5/1971 | Morgan | |
| 3,710,789 A | 1/1973 | Ersek | |
| 3,720,959 A | 3/1973 | Hahn | |
| 3,805,300 A | 4/1974 | Tascon-Alonso et al. | |
| 3,849,805 A | 11/1974 | Leake et al. | |
| 3,955,567 A | 5/1976 | Richmond et al. | |
| 4,164,794 A * | 8/1979 | Spector et al. | 623/23.6 |
| 4,186,448 A * | 2/1980 | Brekke | 128/898 |
| 4,344,191 A | 8/1982 | Wagner | |
| D270,373 S | 8/1983 | Straith | |
| 4,484,570 A | 11/1984 | Sutter et al. | |
| 4,502,161 A | 3/1985 | Wall | |
| 4,636,215 A | 1/1987 | Schwartz | |
| D290,877 S | 7/1987 | Giampapa et al. | |
| D290,878 S | 7/1987 | Giampapa et al. | |
| D290,879 S | 7/1987 | Giampapa et al. | |
| 4,693,722 A | 9/1987 | Wall | |
| 4,704,126 A * | 11/1987 | Baswell et al. | 623/10 |
| 4,713,077 A | 12/1987 | Small | |
| 4,726,808 A | 2/1988 | Collins | |
| 4,731,082 A | 3/1988 | Giunta | |
| 4,756,862 A * | 7/1988 | Spector et al. | 264/126 |
| 4,778,472 A | 10/1988 | Homsy et al. | |

(Continued)

FOREIGN PATENT DOCUMENTS

DE 4414675 C1 9/1995

(Continued)

OTHER PUBLICATIONS

Hoshi M. Bhathena, Primary Reconstruction of Mandible in Head and Neck Cancer with Silastic Implant—A Review of 69 Cases, 2 Acta Chirurgiae Plasticae 40, 31-35, (1998).

(Continued)

*Primary Examiner*—Anu Ramana
(74) *Attorney, Agent, or Firm*—Woodcock Washburn LLP (57) ABSTRACT

An orthopedic tissue spacer comprising a body portion having first and second ends, an outer surface and a longitudinal axis, at least one of the ends configured to engage a first bone segment, wherein at least a portion of the body portion is flexible and the outer surface is configured to resist tissue adhesion thereto.

44 Claims, 6 Drawing Sheets

U.S. PATENT DOCUMENTS

| | | | |
|---|---|---|---|
| 4,787,906 A | 11/1988 | Haris | |
| 4,790,849 A | 12/1988 | Terino | |
| 4,888,018 A | 12/1989 | Giampapa | |
| 4,917,701 A | 4/1990 | Morgan | |
| 4,969,901 A | 11/1990 | Binder | |
| 4,990,160 A | 2/1991 | Terino | |
| 5,084,051 A | 1/1992 | Toermaelae et al. | |
| D326,157 S | 5/1992 | Giunta | |
| 5,139,497 A | 8/1992 | Tilghman et al. | |
| D329,700 S | 9/1992 | Terino | |
| D330,421 S | 10/1992 | Mittelman | |
| D330,422 S | 10/1992 | Mittelman | |
| 5,195,951 A | 3/1993 | Giampapa | |
| 5,201,736 A | 4/1993 | Strauss | |
| 5,201,737 A | 4/1993 | Leibinger et al. | |
| D340,982 S | 11/1993 | Terino | |
| 5,380,328 A | 1/1995 | Morgan | |
| 5,380,329 A | 1/1995 | Elia et al. | |
| 5,383,931 A | 1/1995 | Hehli et al. | |
| 5,413,577 A | 5/1995 | Pollock | |
| 5,413,600 A | 5/1995 | Mittelman | |
| 5,421,831 A | 6/1995 | Giampapa | |
| 5,468,242 A | 11/1995 | Reisberg | |
| 5,489,305 A | 2/1996 | Morgan | |
| 5,492,697 A | 2/1996 | Boyan et al. | |
| 5,496,371 A | 3/1996 | Eppley et al. | |
| 5,501,706 A | 3/1996 | Arenberg | |
| 5,503,164 A | 4/1996 | Friedman | |
| 5,514,179 A | 5/1996 | Brennan | |
| 5,545,226 A | 8/1996 | Wingo et al. | |
| 5,549,620 A | 8/1996 | Bremer | |
| 5,549,680 A | 8/1996 | Gordon | |
| 5,554,194 A | 9/1996 | Sanders | |
| 5,569,250 A | 10/1996 | Sarver et al. | |
| 5,578,036 A | 11/1996 | Stone et al. | |
| 5,658,516 A | 8/1997 | Eppley et al. | |
| 5,683,459 A * | 11/1997 | Brekke | 424/423 |
| 5,690,631 A | 11/1997 | Duncan et al. | |
| 5,707,373 A | 1/1998 | Sevrain et al. | |
| 5,725,549 A * | 3/1998 | Lam | 623/1.15 |
| 5,728,157 A | 3/1998 | Prescott | |
| 5,766,176 A | 6/1998 | Duncan | |
| 5,769,637 A * | 6/1998 | Morgan | 433/176 |
| 5,800,436 A | 9/1998 | Lerch | |
| 5,814,048 A | 9/1998 | Morgan | |
| 5,824,088 A | 10/1998 | Kirsch | |
| 5,863,297 A | 1/1999 | Walter et al. | |
| 5,876,447 A | 3/1999 | Arnett | |
| 5,882,351 A | 3/1999 | Fox | |
| 5,895,387 A | 4/1999 | Guerrero et al. | |
| 5,895,427 A * | 4/1999 | Kuslich et al. | 128/898 |
| 5,899,939 A | 5/1999 | Boyce et al. | |
| 5,919,234 A | 7/1999 | Lemperle et al. | |
| 5,961,519 A | 10/1999 | Bruce et al. | |
| 5,975,904 A | 11/1999 | Spiegel | |
| 5,980,540 A | 11/1999 | Bruce | |
| 5,989,292 A | 11/1999 | Van Loon | |
| 6,022,351 A | 2/2000 | Bremer et al. | |
| 6,053,919 A | 4/2000 | Talos et al. | |
| 6,060,641 A | 5/2000 | Manolidis | |
| 6,068,631 A | 5/2000 | Lerch | |
| 6,071,291 A | 6/2000 | Forst et al. | |
| 6,090,999 A | 7/2000 | Bruce et al. | |
| 6,093,201 A | 7/2000 | Cooper et al. | |
| 6,123,731 A | 9/2000 | Boyce et al. | |
| 6,126,663 A | 10/2000 | Hair | |
| 6,143,036 A | 11/2000 | Comfort | |
| 6,168,631 B1 * | 1/2001 | Maxwell et al. | 623/21.18 |
| 6,176,879 B1 | 1/2001 | Reischl et al. | |
| 6,197,037 B1 | 3/2001 | Hair | |
| 6,206,882 B1 | 3/2001 | Cohen | |
| 6,221,075 B1 | 4/2001 | Tõrmälä et al. | |
| RE37,249 E | 6/2001 | Leibinger et al. | |
| 6,254,639 B1 | 7/2001 | Peckitt | |
| 6,258,091 B1 | 7/2001 | Sevrain et al. | |
| 6,270,500 B1 | 8/2001 | Lerch | |
| 6,277,150 B1 | 8/2001 | Crawley et al. | |
| 6,280,473 B1 | 8/2001 | Lemperle et al. | |
| 6,293,967 B1 * | 9/2001 | Shanley | 623/1.15 |
| 6,294,041 B1 | 9/2001 | Boyce et al. | |
| 6,294,187 B1 | 9/2001 | Boyce et al. | |
| 6,328,743 B2 | 12/2001 | Lerch | |
| 6,328,765 B1 | 12/2001 | Hardwick et al. | |
| 6,355,044 B1 | 3/2002 | Hair | |
| 6,371,987 B1 * | 4/2002 | Weiland et al. | 623/17.11 |
| 6,379,363 B1 | 4/2002 | Herrington et al. | |
| 6,391,059 B1 | 5/2002 | Lemperle et al. | |
| 6,409,764 B1 | 6/2002 | White et al. | |
| 6,461,385 B1 | 10/2002 | Gayer et al. | |
| 6,491,725 B1 | 12/2002 | Koyama et al. | |
| 6,511,482 B1 | 1/2003 | Wellisz et al. | |
| 6,544,266 B1 | 4/2003 | Roger et al. | |
| 6,572,623 B1 | 6/2003 | Birchall et al. | |
| 6,582,435 B2 | 6/2003 | Wellisz et al. | |
| 6,589,244 B1 | 7/2003 | Sevrain et al. | |
| 6,599,323 B2 | 7/2003 | Melican et al. | |
| 6,767,367 B1 * | 7/2004 | Michelson | 623/17.16 |
| 7,156,880 B2 * | 1/2007 | Evans et al. | 623/23.51 |
| 7,166,133 B2 * | 1/2007 | Evans et al. | 623/23.51 |
| 2001/0002446 A1 | 5/2001 | Plouhar et al. | |
| 2001/0011173 A1 | 8/2001 | Lerch | |
| 2001/0014831 A1 | 8/2001 | Scarborough | |
| 2001/0018614 A1 | 8/2001 | Bianchi | |
| 2001/0043940 A1 | 11/2001 | Boyce et al. | |
| 2002/0004660 A1 | 1/2002 | Henniges et al. | |
| 2002/0004661 A1 | 1/2002 | Sevrain et al. | |
| 2002/0016593 A1 | 2/2002 | Hearn et al. | |
| 2002/0040224 A1 | 4/2002 | Lerch | |
| 2002/0062127 A1 | 5/2002 | Schumacher et al. | |
| 2002/0062128 A1 | 5/2002 | Amis | |
| 2002/0095156 A1 | 7/2002 | Kuras et al. | |
| 2002/0120338 A1 | 8/2002 | Boyer, II et al. | |
| 2002/0120346 A1 | 8/2002 | Boyer, II et al. | |
| 2002/0120347 A1 | 8/2002 | Boyer, II et al. | |
| 2002/0169066 A1 | 11/2002 | Cassidy et al. | |
| 2002/0169455 A1 | 11/2002 | Bannerman et al. | |
| 2002/0177850 A1 | 11/2002 | Bremer | |
| 2003/0023313 A1 | 1/2003 | Byers | |
| 2003/0036760 A1 | 2/2003 | Yeh | |
| 2003/0039676 A1 | 2/2003 | Boyce et al. | |
| 2003/0045935 A1 | 3/2003 | Angelucci et al. | |
| 2003/0083750 A1 | 5/2003 | Schulter | |
| 2003/0100898 A1 | 5/2003 | Wellisz | |
| 2003/0100899 A1 | 5/2003 | Wellisz | |
| 2003/0100900 A1 | 5/2003 | Wellisz | |
| 2003/0100901 A1 | 5/2003 | Wellisz et al. | |
| 2003/0100902 A1 | 5/2003 | Wellisz et al. | |
| 2003/0125743 A1 | 7/2003 | Roman et al. | |
| 2003/0149484 A1 | 8/2003 | Michelson | |

FOREIGN PATENT DOCUMENTS

| | | |
|---|---|---|
| DE | 196 34 697 C1 | 4/1998 |
| EP | 0910993 A2 | 4/1999 |
| EP | 0910993 A3 | 4/1999 |
| EP | 0910993 B1 | 4/1999 |
| EP | FR 2786687 A1 | 6/2000 |
| GB | 2324470 A | 10/1998 |
| JP | 401008965 A | 1/1989 |
| JP | 409173364 A | 7/1997 |
| JP | 409206311 A | 8/1997 |
| JP | 410033578 A | 2/1998 |
| JP | 411155879 A | 6/1999 |
| JP | 2000-135230 A | 5/2000 |

| JP | 2000-139939 A | 5/2000 |
| JP | 20001-39938 A | 5/2000 |
| JP | 2001-161703 A | 6/2001 |
| JP | 2002-045367 A | 2/2002 |
| JP | 2003-038504 A | 2/2003 |
| WO | WO 94/01064 A1 | 1/1994 |
| WO | WO 97/16136 A1 | 5/1997 |
| WO | WO 97/41791 A1 | 11/1997 |
| WO | WO 97/43978 A1 | 11/1997 |
| WO | WO 98/46153 A1 | 10/1998 |
| WO | WO 01/72244 A1 | 10/2001 |

OTHER PUBLICATIONS

G.F. Gregory and D.V. Gavin, *Improving the Mandibular Reconstruction Plate: Technical Innovation*, 45 J.R. Coll. Surg. Edinb., 120-21 (2000).

Lawrence A. Weinberg, *Treatment Prostheses in TMJ Dysfunction-Pain Syndrome*, 39 The Journal of Prosthetic Dentistry, 654-69 (1978).

Franklin H. Sim, *Replacement of the Proximal Humerus with a Ceramic Prosthesis: A Preliminary Report*, 146 Clinical Orthopaedics and Related Research, 161-74 (1980).

Ulrich T. Hinderer, *Malar Implants for Improvement of the Facial Appearance*, 56 Plastic & Reconstructive Surgery, 157-65 (1975).

James Baker Jr., *Repair of Concavity of Thoracic Wall with Silicone Elastomer Implant*, 56 Plastic & Reconstructive Surgery, 212-15 (1975).

K. Ogata, *The Influence of Spacers on Forces Exerted on the Abutment Teeth of Complete Mandibular Overdentures*, 17 Journal of Oral Rehabilitation, 269-78 (1990).

K. Lekkes, *Absolute Augmentation of the Mandible*, 6 Int J. Oral Surg., 147-52 (1977).

Zoran Cupic, *Long-Term Follow-Up of Charnley Arthroplasty of the Hip*, 141 Clinical Orthopaedics and Related Research, 28-43 (1979).

* cited by examiner

SOFT TISSUE SPACER

FIELD OF THE INVENTION

The present invention relates to the field of treating a removed area of tissue or bone with an implant, methods of treating a removed area of diseased, damaged, or defective bone and/or tissue with an implant, systems of combining an implant with a bone plate, kits including implants, and the implants themselves. More particularly, a soft tissue spacer is provided as a flexible implant for temporarily remaining in a resection cavity during treatment of the resection area. The invention may be particularly useful in procedures involving removal of at least a portion of a bone and tissue and subsequent treatment thereof, but the invention may be used in other suitable areas of the body as well.

BACKGROUND OF THE INVENTION

The use of implants for a variety of prosthetic procedures is widely accepted in numerous fields. In some cases, diseased, damaged, or defective bone and/or tissue, such as malignant tumors, may require removal of the afflicted tissue and bone. Where the resection cavity is large, an implant may be inserted to occupy the space left by the removed tissue or bone. Some cases require the introduction of a permanent implant which remains in the resection cavity indefinitely. It is generally desirable that such an implant be of sufficient strength and biocompatibility to coexist and integrate with adjacent remaining tissue and bone. Implants for replacing bone are typically autografts, allografts, or ceramics such as calcium phosphate or calcium sulfate, or metals such as stainless steel or titanium.

The desired advantages of permanent implants can also lead to drawbacks. For instance, while many permanent implants are constructed of load-bearing materials, implants made of such materials may not react well to procedures such as radiation treatment. Metal implants may act as a "lens" during radiation treatment, effectively refocusing and intensifying radiation waves onto to a small location on the patient's or surgeon's body. Autografts require lengthy procedures (e.g. harvesting, shaping, and implantation) and thus time constraints may not allow their use.

Permanent autografts and allografts may react poorly to chemotherapy treatments. Chemotherapy aims to kill cancer cells, as they are normally weaker than surrounding healthy cells. However, typically the cells in autografts and allografts are of a somewhat weakened state when inserted in a resection cavity. Therefore, chemotherapy can have the adverse effect of destroying the autograft or allograft cells themselves, thereby weakening the permanent implant and rendering it less effective. Furthermore, if the patient has poor blood supply in the affected area, allografts and autografts may not be effective.

Thus, a temporary implant may be used to occupy a resection cavity left by the removal of the afflicted area of tissue and bone. A permanent implant (i.e. allograft or autograft) may eventually be used, but it may be desirable to conclude treatments such as radiation or chemotherapy before installing them. Temporary implants used in this manner may assist surgeons by maintaining the size of the resection cavity from the time of the first removal of bone and/or tissue to the time of the permanent implant introduction and placement. If the cavity were left unfilled during the chemotherapy or radiation therapy period, the soft tissue surrounding the site could intrude into the cavity left by the primary removal of bone and/or tissue, thereby interfering with subsequent installation of a permanent implant. Thus, a temporary implant would provide the advantage of resisting such soft tissue intrusion, while also providing a short term cosmetic replacement body to approximate the patient's original anatomy during the chemotherapy or radiation period.

SUMMARY OF THE INVENTION

An orthopedic tissue spacer is provided comprising a body portion have first and second ends, an outer surface and a longitudinal axis, at least one of the end configured to engage a first bone segment, wherein at least a portion of the body portion is flexible and the outer surface is configured to resist tissue adhesion thereto.

The flexibility of the body portion may be achieved by providing at least one recess through at least a portion of the body. At least one recess may have a depth les than a cross-sectional dimension of the spacer. At least one recess may further have a length, wherein the depth of the recess is variable along the length of the recess. The body portion may have a plurality of recesses, wherein at least two recesses have different dimensions. The body portion may also have a plurality of recesses, wherein the recesses are approximately equally spaced along the longitudinal axis of the spacer.

The biocompatible material of the spacer may also be bioinert. The biocompatible material may also be Ultra High Molecular Weight Polyethylene (UHMWPE) or Poly Ether Ether Ketone (PEEK). The biocompatible material may also be capable of resisting tissue ingrowth and/or adhesion.

The body portion may further comprise an outer surface that is generally elliptical in cross-section, or shaped to approximate the cross section of the resected bone.

The ends of the spacer may have different shapes from one another. Each end may have a shape that substantially conforms to a contacted bone segment.

At least a portion of the spacer may be coated with at least one therapeutic agent. The therapeutic agent may be an antibiotic or an antiseptic. The therapeutic agent may be applied by spraying, dipping, soaking, impregnating, or chemical vapor deposition, or a combination thereof. The therapeutic agent may be selected from a group comprising IGF (insulin-like growth factors), TGF (transforming growth factors), FGB (fibroblast growth factors), EGF (epidermal growth factors), BMP (bone morphogenic proteins) and PDGF (platelet-derived growth factors).

The spacer may have a bore, the bore having a longitudinal axis substantially parallel or non-parallel to that of the body portion. The bore may comprise about 90% of the cross sectional area of the spacer. The thickness of the bore may also be substantially smaller than the corresponding thickness of the ends. The spacer may also have a plurality of bores suitable for accepting at least one suture.

The spacer may further comprise an outer surface, and a bore having an inner surface than substantially conforms to the shape of the outer surface.

The spacer may be preformed in a preselected shape. The preselected shape may be configured to substantially mimic at least a portion of removed bone. The removed bone may be a portion of a human mandible.

At least a portion of the body portion of the spacer may have a dull finish or a roughened finish to reduce glare in the surgical work site. At least one end of the spacer may also have a roughened finish to enhance engagement of the end with the associated bone segment.

A method of treating a resection cavity is also disclosed, comprising the steps of (a) removing a first amount of tissue from a body site, at least a portion of the tissue being diseased, damaged, or defective, thereby leaving a cavity, (b) selecting a first spacer for temporary introduction into a cavity, (c) placing the first spacer into the cavity, and (d) performing at least one treatment on the body site.

The method may also comprise the removal of bone from the body site. A second amount of bone or tissue may also be removed. The spacer may also be removed from the cavity after a treatment. A second spacer may be selected and placed for permanent introduction into the cavity.

A portion of the spacer may be removed prior to use. The spacer may be flexed prior to use, in order to better conform to a body site. The spacer may be flexed so that upon insertion, the ends of the spacer impart forces on at least a portion of the cavity.

A bone plate may be attached adjacent to the body site prior to insertion of the spacer. The spacer may be fixed attached to the bone plate.

The treatment of the method may consist of chemotherapy and/or radiation treatment.

The spacer may be sutured to the adjacent bone or tissue after insertion.

A system of treating a resection cavity is also disclosed, comprising a spacer having a body portion comprised of a biocompatible material having first and second sides, and a central longitudinal axis; wherein at least one of the sides is a bone engaging side; wherein at least a portion of the body portion may be flexed by an external force; and a least one plate fixedly attached to the spacer.

The bone plate may be attached to the spacer with an adhesive. The bone plate may be attached to the spacer with a fastener. Accordingly, the spacer may have at least one bore for receiving a fastener.

A kit is also disclosed, comprising a plurality of spacers, at least one bone plate; wherein at least one spacer is selected for temporary introduction into a resection cavity. The kit may also contain at least one fastener, or at least one tool. The tool may be an alignment instrument or a cutting instrument.

The dimensions of the spacer may vary based primarily on the size of the resection cavity to be occupied. In most instances, the spacer shape will be chosen to best replicate the size and shape of the tissue and bone removed during the resection procedure.

The spacer may be modified or otherwise customized during surgery to precisely fit the individual patient's resection cavity. A custom shaped implant may also be manufactured to fit the individual patient based on information taken by CT or MRI imaging of at least a portion of the patient prior to surgery.

The recesses may be of a variety of configurations and depths. In one embodiment, at least one recess has a depth less than the distance between the front side and rear side. In another embodiment, at least one recess has a depth equal to the distance between the front side and rear side. The depth and corresponding volume of each recess is at least in part determinative of the flexibility of the spacer at the particular location of each recess. Moreover, the depth of a single recess may vary along the longitudinal axis of the recess. For instance, this option may be utilized when deeper recesses are sought near the center of the spacer, but shallower cuts are required around the ends of the spacer.

At least two recesses in a single spacer may each have different dimensions. Further, all recesses in a single spacer may be of a different size and shape than any other recess in the same spacer. Any combination or pattern of recesses is contemplated to allow surgeons to utilize spacers that best fit the desired physical characteristics of the resection cavity.

The recesses in the front side may be substantially parallel and approximately equally spaced along the longitudinal axis of the spacer. The depth, width, and length of the recesses, however, may vary depending on numerous factors, including the dimensions of the spacer and the amount of flexibility desired by the surgeon.

The first resection procedure may encompass the removal of tissue, bone, or both. Subsequently resection procedures may be necessary to remove the desired amount of tissue, bone, or both. Any subsequent resection procedures may occur at any time after the first resection procedure.

The selection of the first spacer may also occur prior to the step of performing the first resection procedure. This option provides the surgeon with an estimate of the final cavity size and shape, before beginning the first resection procedure.

The first spacer may also be removed after the treatment has occurred. At this time, the surgeon may be ready to fit the cavity with a permanent implant. Alternatively, the surgeon may feel it is necessary to conduct another resection procedure.

After the first spacer is removed, a second spacer may also be selected to be introduced to the cavity and subsequently placed within the cavity. The second spacer may be temporary or permanent.

BRIEF DESCRIPTION OF THE DRAWINGS

Numerous features of the present invention are disclosed in the accompanying drawings, wherein similar reference characters denote similar elements throughout the several views, and wherein.

DETAILED DESCRIPTION OF THE PREFERRED EMBODIMENTS

Figure 1:
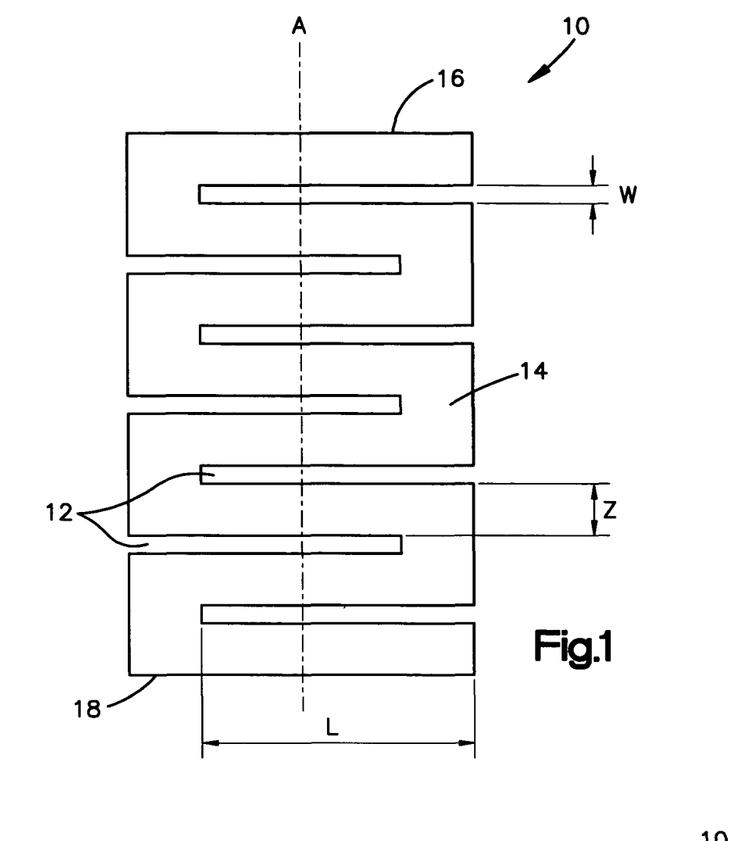
FIG. 1 is a top view of a first exemplary embodiment of the spacer according to the present invention.
Figure 2:
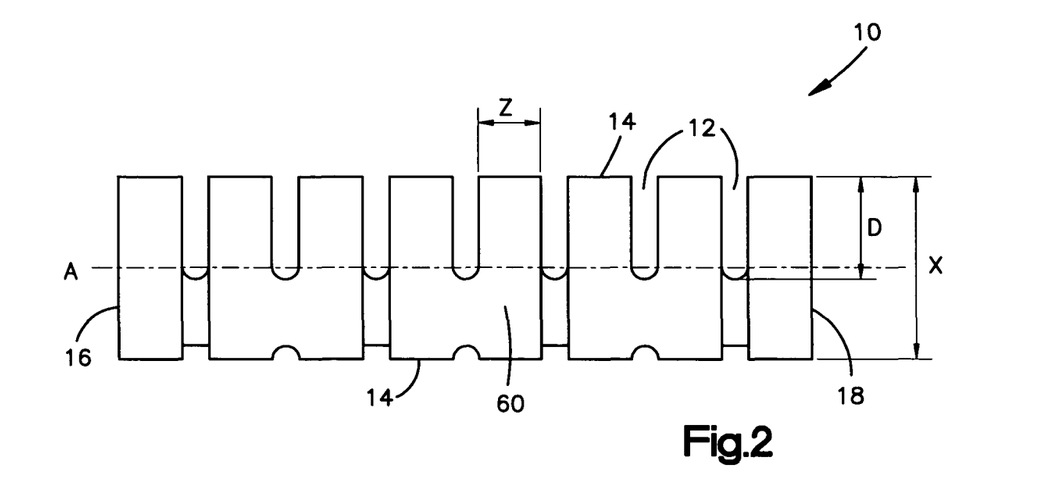
FIG. 2 is a side view of the spacer of FIG. 1.

Referring to FIGS. 1-2, there is shown an exemplary non-structural solid spacer 10 for use as a temporary soft tissue spacer in a human body. In particular, the spacer 10 may be configured to be placed between, for example, cut bone ends obtained as a result of the removal of a damaged or diseased portion of bone. As previously noted, a temporary spacer may be used where additional therapeutic treatments will be performed on the patient in the resection area (e.g. chemotherapy, radiation), since such treatments may hinder reintegration of a permanent spacer such as allograft (i.e. bone). The spacer 10 may have physical characteristics (size and shape) similar to those of the replaced bone and tissue (and the permanent implant) so as to provide the patient with as normal an appearance as possible during the subsequent treatment period.

Thus the spacer 10 may have an outer surface 14 and first and second bone engaging ends 16, 18 and an axis A. The surfaces and ends of the spacer 10 may be flat, curved or may take on any appropriate shape to provide a desired overall shape of the spacer. The outer surface 14 and ends 16, 18 may be roughened to improve the retention of the spacer 10 within the resection cavity 70.

The relief cuts 12 in the spacer 10 may allow the spacer to bend, expand, or contract to closely fit the occupied cavity. The spacer 10 may be bent, expanded, or contracted along at least one axis. In the embodiment illustrated in FIG. 1, the relief cuts 12 are substantially parallel to each other and are approximately equally spaced along the longitudinal axis A of the spacer 10. The relief cuts 12 are also oriented substantially perpendicular to the longitudinal axis A, thus allowing expansion or contraction of the spacer 10. The positioning of the relief cuts 12 may be varied in width, length and angular orientation, depending at least in part by the amount of flexibility desired from the spacer 10 and the overall size and shape of the spacer 10. The relief cuts 12 may have three dimensions: length L, width W, and depth D. Each dimension may be varied depending on the amount and/or direction of flexibility desired and the overall size and shape of the spacer 10. For example, the length L may vary from 0.1 mm to 30 mm. The width W may be about 0.1 mm or greater. The depth D may vary from 0.1 mm to 20 mm. Thus, each of the dimensions L, W and D may be from about 0% to about 90% of the corresponding spacer dimension. The distance Z between relief cuts 12 may also be varied. The dimensions of the relief cuts 12 also may be varied between separate relief cuts 12 in a single spacer 10. Further, the dimensions of a single relief cut 12 may be varied within a single relief cut 12 as well. For instance, it may be preferable to vary the depth D of a relief cut 12 along its length L to provide a deeper relief cut 12 near the center of the spacer 10 and a consequently shallower relief cut 12 near the edges of the spacer 10. Such an arrangement may provide the spacer 10 with greater flexibility along its longitudinal axis A and less flexible along its edges. For example, where the spacer 10 will be used to approximate a curved portion of the mandible, the spacer may have relief cuts 12 configured to allow the spacer 10 to be flexed in a direction that would allow approximation of the mandible curvature, but would provide stiffness in a perpendicular direction. Likewise, the width W of a particular relief cut may be varied along its length L to provide additional flexibility in a desired direction. As will be apparent to one of ordinary skill in the art, the inventive spacer 10 may incorporate any combination of relief cuts 12 having any of a variety of dimensions as desired to provide a spacer 10 having a desired flexibility for fitting a particular targeted anatomical resection cavity.

In one embodiment, the spacer 10 may have general cross-sectional dimensions of from about (20 mm by 8 mm) to about (30 mm by 12 mm). In the embodiment, illustrated in FIGS. 1-2, the relief cuts 12 may extend to a depth D approximately equal to one-half the height X of the spacer 10. The depth D is also consistent among all relief cuts 12 in this embodiment. However, the depth D of the relief cuts 12 may be less than half of the distance X. Also, the depth D of the relief cuts 12 may be a distance greater than half the distance X. In yet another embodiment, the relief cuts 12 may extend completely through the body 60 of the spacer 10 as to create a relief cut 12 that passes from the outer surface 14 at one point, through the body 60, and out the outer surface 14 at another point. As previously noted, it may be desirable have several relief cut 12 depth D options, because the relief cut depth D at least in part may contribute to the amount of flexibility the spacer 10 has.

Figure 3:
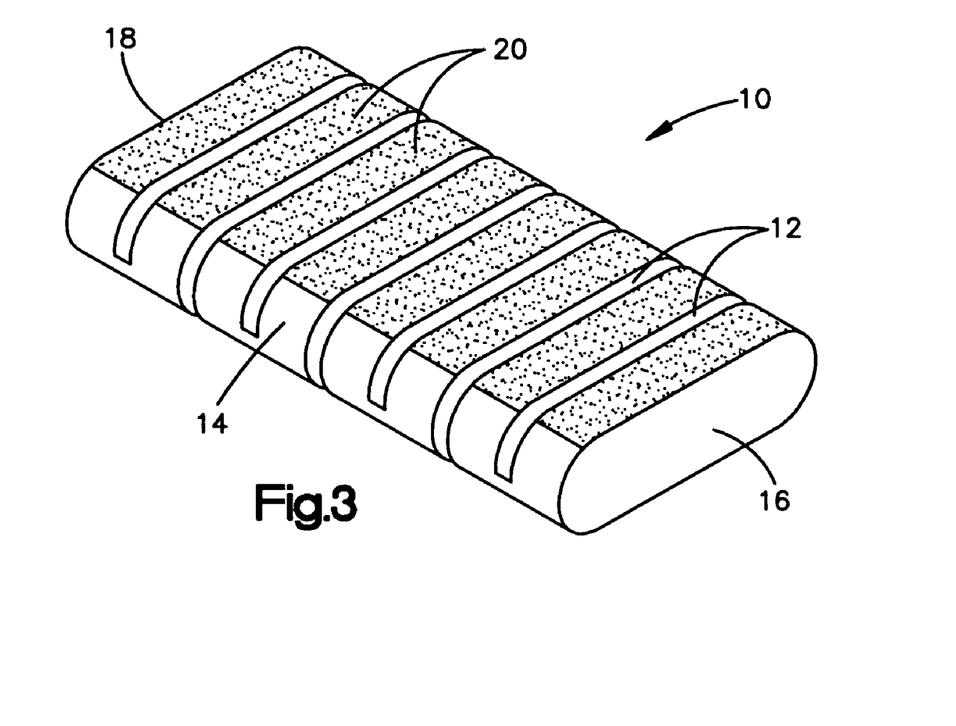
FIG. 3 is a perspective view of the spacer of FIG. 1, showing at least a portion of the spacer coated by a therapeutic agent and further showing an end having a generally elliptical shape.

As illustrated in FIG. 3, the spacer may have at least two ends 16, 18, each of which may have a generally elliptical shape. However, the ends 16, 18 may be of any desired shape or dimension to create the desired shape of the spacer 10 as a whole. Moreover, the ends 16, 18 may be of different shapes from one another. Accordingly, the cross-sectional shape and dimensions of the spacer 10 may vary over the longitudinal axis A, at least in part as a function of dimensional differences in the ends 16, 18. Providing a spacer with a varying cross-sectional shape may be desirable to allow a more precise fit between spacer 10 and an irregular-shaped resection cavity 70.

Figure 4:
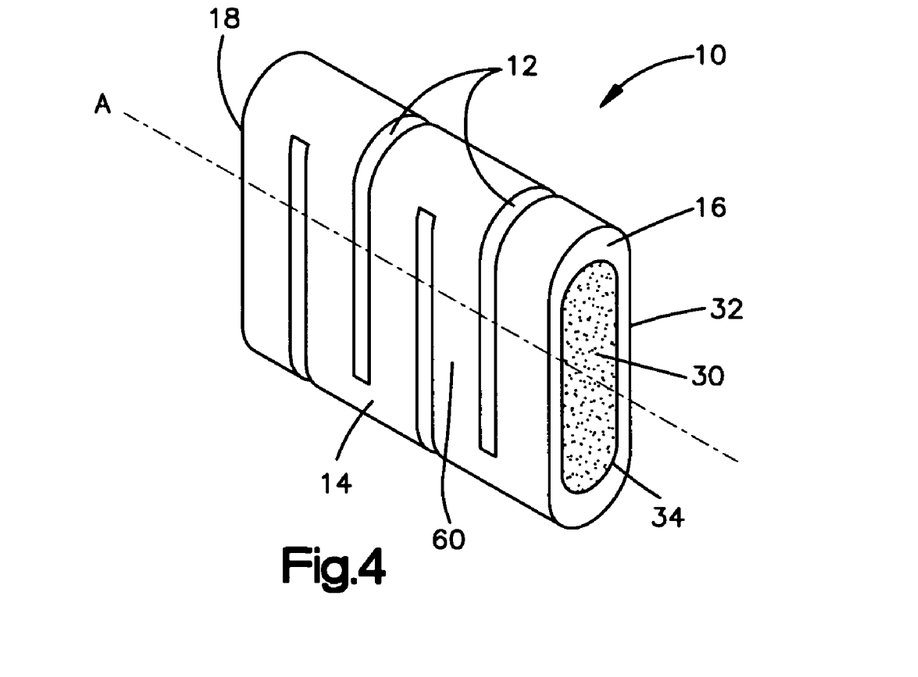
FIG. 4 is a perspective view of a second embodiment of a spacer with a bore running through the longitudinal axis of the spacer.

Referring to FIG. 4, a spacer 10 may have a bore 30 with an axis C (not shown) substantially collinear to the longitudinal axis A of the spacer 10. The bore 30 may provide the spacer 10 with enhanced flexibility as compared to the previously described embodiments. The bore 30 also may make the spacer 10 lighter. These features may be particularly advantageous where the spacer 10 is made of a metal, which may be inherently stiffer and heavier than a non-metallic material.

In one embodiment, the size and shape of the bore 30 may approximate the shape of the outer edge 32 of the spacer 10, so as to maintain a generally consistent thickness T of the spacer 10. Thus the spacer 10 may be provided having a thickness T in the range of from about 1.5 mm to about 5 mm. It should be noted that a constant thickness T is not critical, and thus a spacer having a varying thickness T along its length may also be provided. Thus, the bore 30 may be of any shape of size appropriate to provide a spacer 10 of desired flexibility. For example, the outer edge 32 shape may be elliptical, while the inner edge 34 shape may be circular, square, etc. The cross-sectional shape and size of the bore 30 may also vary along the length of the longitudinal axis A. The bore 30 may comprise at least one channel for passing an object, such as a suture, cable or other support, through at least a portion of the body 60 of the spacer 10. Additionally, more than one bore 30 may be provided in a single spacer 10.

Figure 5A:
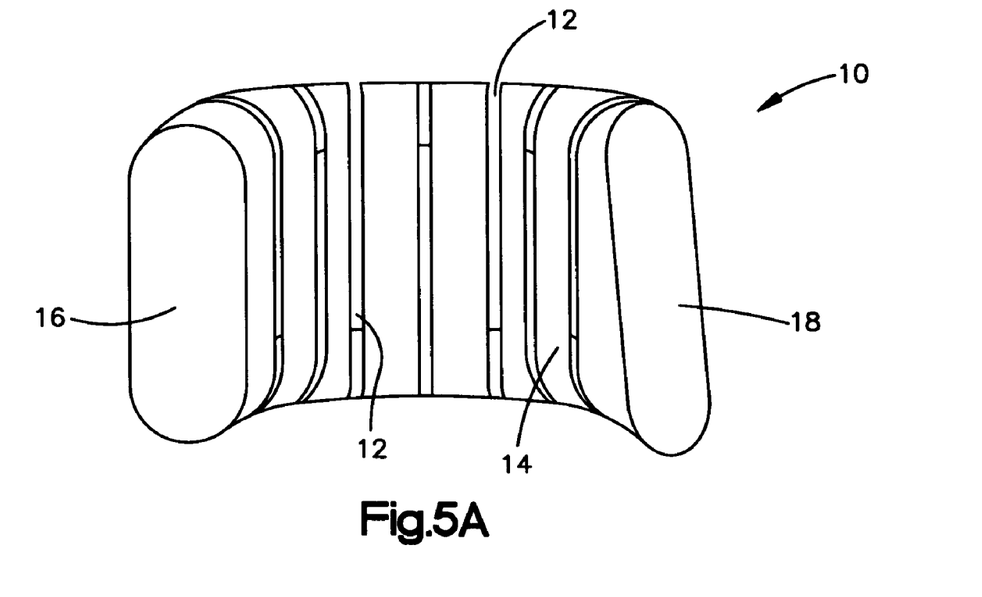
FIG. 5A is a side view of a third embodiment of a spacer having a preformed curvature.
Figure 5B:
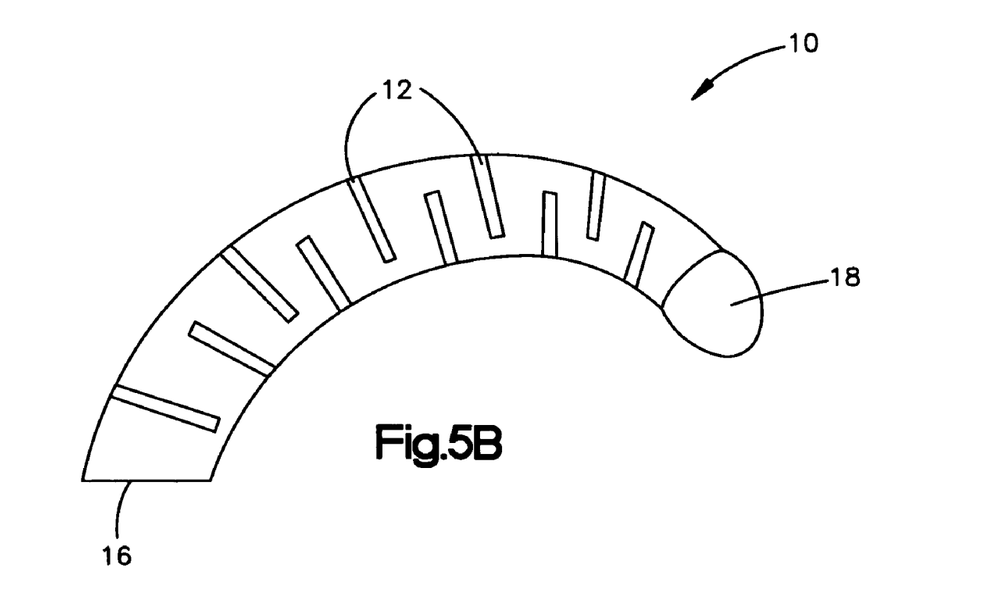
FIG. 5B is a top view of the spacer of FIG. 5A.

FIGS. 5A-7B show several views of a spacer 10 having a variety of preformed shapes. The spacer 10 of FIG. 5A is a generally concave design, which may be useful in an irregular resection cavity 70, where the cavity results as a result of "carving out" diseased or damaged bone in the shape of an trough. The dimensions of individual relief cuts 12 may vary depending at least in part on the location of a relief cut 12 in relation an axis for displacement. FIG. 5B is a top view of the spacer 10 in FIG. 5A.

Figure 6A:
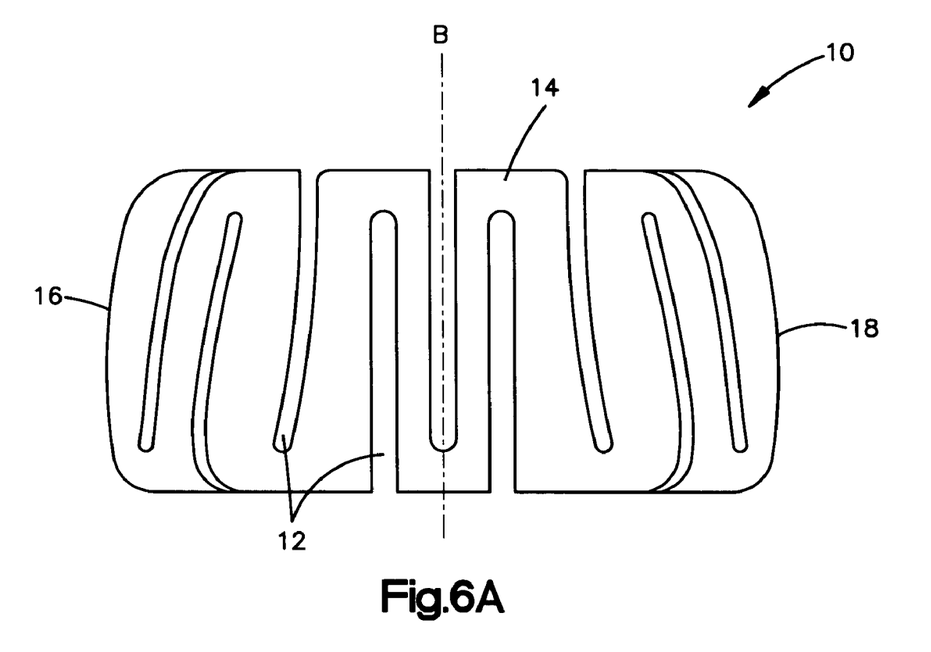
FIG. 6A is a side view of a fourth embodiment of a spacer having a preformed curvature, displaced around axis B.
Figure 6B:
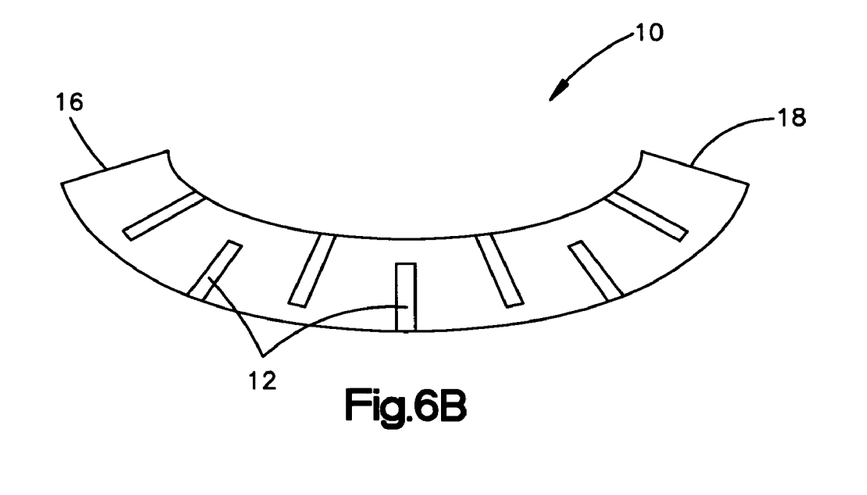
FIG. 6B is a top view of the spacer of FIG. 6A.

The spacer 10 of FIG. 6A is a generally convex design shown from a side view. This particular design may be useful for temporarily replacing the front section of a human mandible 50. In this embodiment, the spacer 10 is displaced around the axes B. FIG. 6B is a top view of the spacer 10 of FIG. 6A.

Figure 7A:
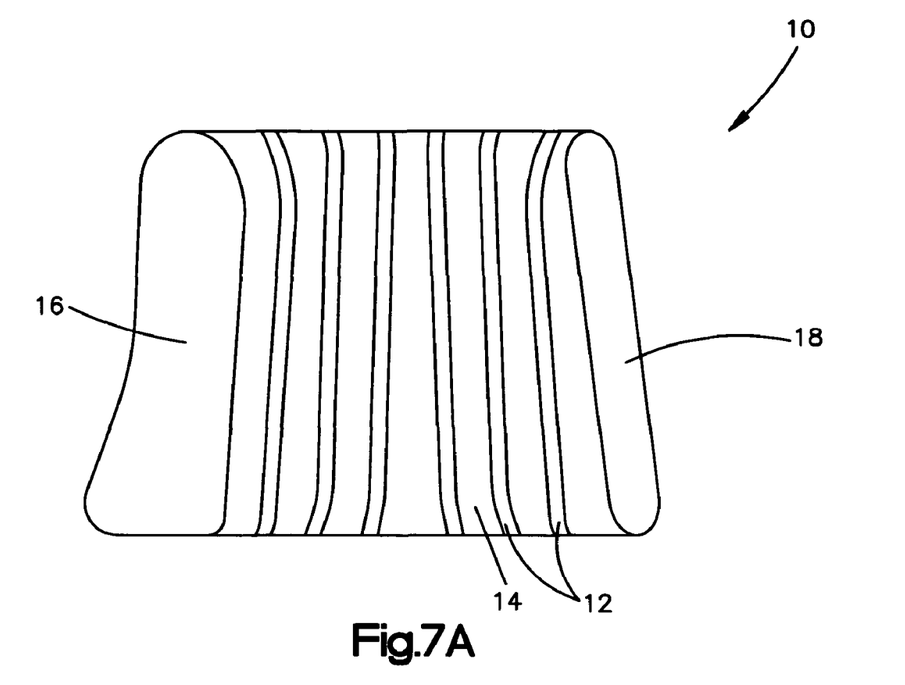
FIG. 7A is a side view of a fifth embodiment of a spacer having a curved preformed shape with at least one end conforming to that of a part of a mandible and an angled opposite end.
Figure 7B:
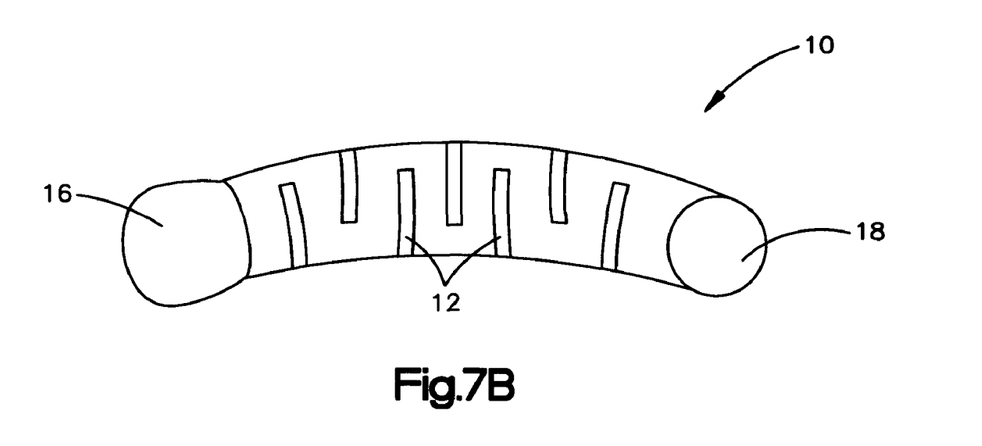
FIG. 7B is a top view of the spacer of FIG. 7A.
Figure 8:
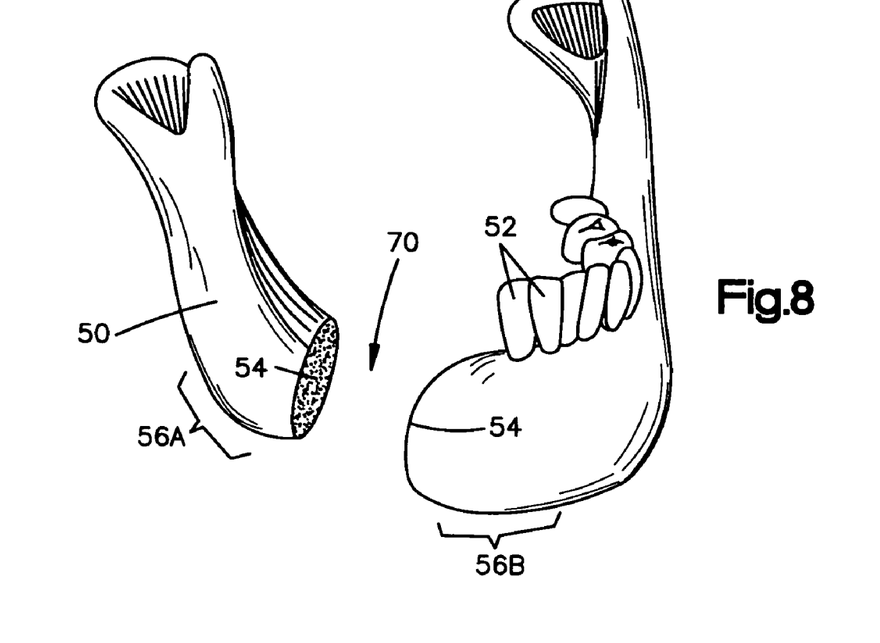
FIG. 8 is a perspective view of a mandible with a resection cavity.

The spacer 10 of FIG. 7A is an irregular design shown from a side view. This embodiment may be used to temporarily replace a portion of the midsection of a human mandible 50 (as seen in FIG. 8), in which the lateral boundaries of the resection cavity 70 are irregularly-shaped bone walls 54. In this embodiment, the first side 16 is shaped to generally conform to the irregular cross-sectional shape of a mandible, while the second side is angled. FIG. 7B is a top view of the spacer 10 of FIG. 7A. Generally, the spacer 10 may have a preformed shape to generally correspond to the intended use and/or positioning of the spacer 10. The outer surface 14, and ends 16, 18 may also be individually preformed to more closely fit the bone ends of the targeted bone cavity 70.

To allow even further conformity of the spacer 10 to the resection cavity, the surgeon may alter the shape or design of a spacer 10 to fit the particular anatomy of the patient. Thus, the surgeon may remove at least a portion of the spacer 10 prior to use. This may occur, for example, by a surgeon cutting off at least a portion of one or both ends 16, 18 of the spacer 10, or by removing a portion or portions of the body of the spacer. A surgeon may also cut custom relief cuts 12 in a spacer, or alter existing relief cuts 12 to make them deeper or longer. The shape of the spacer may be altered using any of a variety of standard surgical tools such as burrs, reciprocating saws, drills, etc., that are available to a surgeon in the operating room. A surgeon may alter the shape of a spacer 10 regardless of whether or not the spacer 10 is preformed.

Referring to FIG. 8, an exemplary patient mandible 50 is shown having teeth 52 and a resection cavity 70. The illustrated resection cavity 70 may be the result of a procedure involving the removal of diseased or defective tissue and/or bone, however other procedures (e.g. cosmetic reshaping) are also contemplated, such as where a patient suffers from a congenital deformity or bone deficit. Walls 54 may define at least a portion of the surface area of the resection cavity 70. The shape and total surface area of the walls 54 may depend at least in part on the size and shape of the tissue and/or bone removed during a resection procedure. The contour of surface of the walls 54 may vary as well. Sound bone portions 56A, 56B may remain intact on either side of the resection cavity 70.

Figure 9:
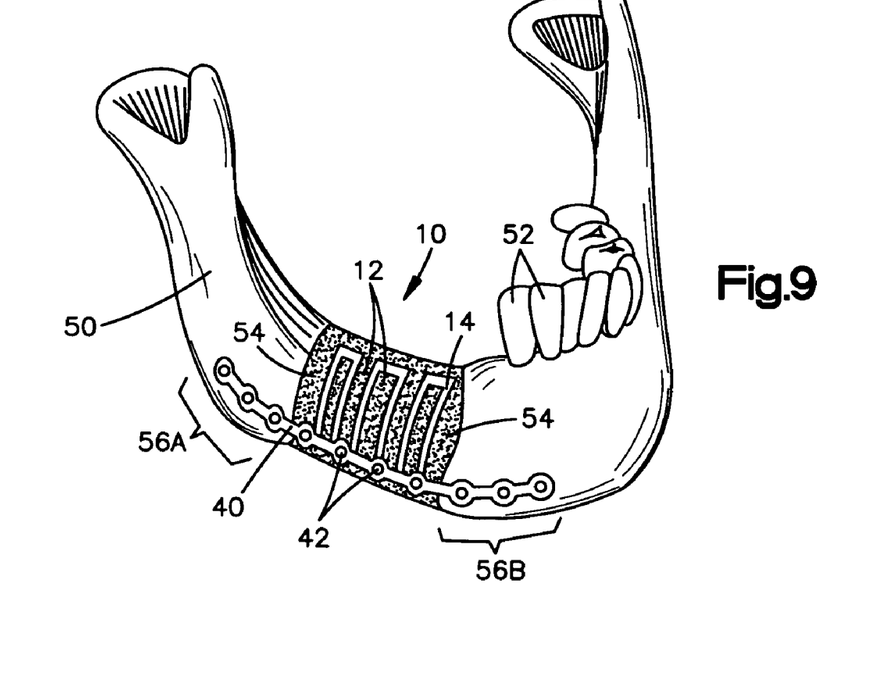
FIG. 9 is a perspective view of the mandible of FIG. 8, to which the spacer of FIG. 1 in combination with a bone plate has been secured.

Referring to FIG. 9, a spacer 10 is illustrated as fixedly attached within a resection cavity 70 in a mandible 50 using a bone plate 40 having fixation holes 44. In this embodiment, the spacer 10 is placed within the resection cavity 70 and the bone plate 40 is fixedly attached (e.g. using bone screws placed in the fixation holes 44) to both the spacer 10 and the mandible 50. The bone plate 40 may be useful for maintaining the spacer 10 within the resection cavity 70 because the spacer 10 itself is not intended to be a load-bearing element. Thus, the spacer may not be able to effectively resist the in-situ forces of musculature and soft tissue without an additional retention device such as a bone plate. The bone plate 40 may therefore assist in preventing the movement or displacement of the spacer 10 by external forces (e.g. chewing or other soft tissue forces) on an exposed portion of the spacer 10 during use. Such displacement may be undesirable because it may allow soft tissue and bone ingrowth into the resection cavity. Further, spacer 10 movement may cause infection in and around the resection cavity 70.

The bone plate 40 may be attached to the spacer 10 and the walls 56A, 56B in a variety of ways. FIG. 9 shows the bone plate 40 fixedly attached to the spacer by fasteners 42 that are received in the spacer 10 by bores. The number, size, and arrangement of fasteners 42 may vary depending at least in part on the size of the bone plate 40 and the securing force necessary to provide adequate immobilization of the spacer 10. However, the bone plate 40 may be attached to the spacer 10 by any appropriate means, including but not limited to screws, nails, clamps, pins, sutures, adhesives, or any combination thereof. The bone plate 40 may have any appropriate number and configuration of fastener holes, and may be flexible or deformable to allow the surgeon to shape the ends of the plate to fit the anatomy of the patient. The plate 40 may be made of any suitable material known in the art, including metals such as titanium or stainless steel, or polymers, resorbable polymers, etc.

Furthermore, although the spacer 10 is described herein as being adapted for fixation to the adjacent bone segments using a bone plate 40, other fixation techniques may also be used. For example, bone screws may be screwed directly through the spacer and into the adjacent bone segments. For such applications, the spacer may have preformed bone screw holes. Alternatively, the spacer may be provided with one or more integral or preformed flaps configured to engage an outer surface of the bone ends. Such flaps may be provided with preformed bone screw holes for screwing the spacer to the adjacent bone. Further, the spacer 10 may be provided with one or more holes suitable for receiving sutures to allow the surgeon to suture the spacer 10 to the surrounding bone and tissue. Such holes may be of any appropriate shape and configuration, and may be angled with respect to the longitudinal axis of the spacer 10 to allow easier threading of suture material through the spacer.

At least a portion of the spacer 10 may be coated with a therapeutic agent 20, which may help prevent infection in the site after the spacer 10 is inserted within the resection cavity 70. The therapeutic agent 20 may be any agent appropriate to prevent infection within the resection cavity 70, including antibiotics and antiseptics. A non-limiting list of therapeutic agents useful in procedures involving spacers includes, but is not limited to, bone growth induction catalysts such as bone morphogenetic proteins, growth factors, peptides, and the like, antivirals, antibiotics, chemotherapy drugs, growth factors, endothelial growth factors, insulin growth factors, or the like, or a combination thereof. Further, the spacer 10 may be coated with more than one therapeutic agent 20. The therapeutic agent 20 may be applied to the spacer 10 by any appropriate means, including but not limited to spraying, impregnating, soaking, dipping, or chemical vapor deposition (CVD). In one embodiment, the therapeutic agent 20 may be applied to the spacer 10 by dipping or soaking the spacer in a dissolved resorbable material such as polylactate which contains a desired concentration of the therapeutic agent 20. A discussion of one manner of application of such therapeutic agents to implants may be found in U.S. Non-provisional patent application Ser. No. 09/801,752, by Schmidmaier et al., filed Mar. 9, 2001, entitled "Biologically Active Implants," the entire contents of which is incorporated herein by reference.

An exemplary method of using the inventive spacer 10 is further provided, with reference to the system depicted in FIG. 9. After identifying a diseased or damaged portion of the anatomy (in this case the mandible 50), the surgeon may remove the affected tissue, along with a small portion of healthy tissue on all sides, leaving a resection cavity 70. The surgeon may then select a spacer 10 for placement in the resection cavity 70. In one embodiment, the spacer 10 may be coated with at least one therapeutic agent 20. The application of therapeutic agent 20 may occur prior to selection or placement of the spacer 10. Prior to inserting the spacer 10 into the resection cavity 70, the surgeon may compress, expand, or in some other way change the shape (e.g., remove at least a portion) of the spacer 10 in order to closely conform it to the resection cavity 70. The spacer 10 may then be inserted into the resection cavity 70. The spacer 10 may be selected to have a length slightly greater than the length of the resection cavity 70, such that when the spacer 10 is inserted into the cavity a small end force is applied to the ends 16, 18 via the walls 54, thus provisionally retaining the spacer 10 within the resection cavity 70. The ends 16, 18 of the spacer 10 therefore may be positioned at least in part against the walls 54 of the resection cavity 70 along the length of the mandible 50. The ends 16, 18 may engage bone or tissue. During the placement, the relief cuts 12 of the spacer 10 may provide flexibility to allow the spacer 10 to expand or compress to occupy the resection cavity 70. Once the spacer is set in the resection cavity 70, at least one bone plate 40 may be fixedly attached to the spacer 10 and the surrounding bone or tissue. Alternatively, the bone plate 40 may be applied to the spacer 10 prior to placing the spacer 10 in the resection cavity 70. The surgeon also may "trial fit" the spacer 10 within the resection cavity 70 by repeatedly inserting and removing the spacer 10 in the resection cavity 70, each time reshaping (cutting) the spacer 10 as required to obtain a desired fit. Once the desired spacer shape is obtained, the spacer 10 and bone plate 40 may be secured to the bone ends 56A, 56B. It is noted that while the spacer 10 is disclosed in combination with a bone plate 40, the spacer 10 may be secured to the bone ends 56A, 56B using any appropriate method, as earlier described. Likewise, the spacer 10 may be used without any additional fixation means.

An additional amount of therapeutic agent 20 may be applied to the spacer 10, bone plate 40, and/or resection cavity 70 at this stage, just prior to closure of the surgical site. This may be preferable due to the loss of some amount of therapeutic agent 20 during the preparation and placement of the spacer 10 in the resection cavity and/or the attachment of the spacer 10 and bone plate 40.

The surgeon may then commence treatment of the surgical site. Examples of such treatment include, but are not limited to, radiation treatment, chemotherapy, isobaric treatments, or the like.

The spacer may also be used simply to allow swelling to subside during the post-operative period and to allow general healing to take place.

After treatment is completed, the surgeon may then re-access the surgical site and remove the spacer 10 and bone plate 40. A permanent implant, such as one made from autograft, allograft, metallic, ceramic, polymer, or other suitable material may then be inserted into the resection cavity 70.

In addition to the disclosed application of the spacer 10 for use in the mandible, the spacer 10 may also be used in other parts of body. One such use is in the hip. In particular, the spacer 10 may be useful to serve as an implant for a resection cavity 70 created by taking a graft from an iliac crest. Such grafts are commonly used in spinal fusion or other bone grafting procedures. Other areas for use of the inventive spacer 10 are any of the bones of the craniofacial region, including the cheekbone.

The spacer 10 may be made of a biocompatible material, for example Ultra High Molecular Weight Polyethylene (UHMW PE). However, the spacer 10 may be constructed out of any appropriate biocompatible material. In addition to UHMW PE, other acceptable biocompatible materials for use with the present invention include, but are not limited to titanium alloys, stainless steel, cobalt chrome alloy and PEEK. The chosen biocompatible material should provide a spacer 10 that can conform or be conformable to opposing bone ends of a resection cavity 70 (see, e.g., FIG. 8) and should be capable of maintaining the cavity relatively free from soft tissue intrusion for an extended period of time, during which a procedure such as radiation or chemotherapy treatments is performed. More specifically, the biocompatible material should be resistant to tissue and bone ingrowth or adhesion while placed in the resection cavity 70. Thus, the spacer 10 should be configured to be readily removable from the resection cavity 70 so that a permanent implant may be easily installed once the radiation or chemotherapy procedures are complete.

The outer surface 14 and ends 16, 18 of the spacer 10 may also be dulled, which may be useful to prevent glare or reflection from the light source of an endoscope used during the procedure.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed:

1. An orthopedic tissue spacer comprising:
   a body portion comprising:
      a front surface, a back surface, and top and bottom surfaces extending between the front and back surfaces, the body portion further defining a first end and a second end;
      a central longitudinal axis extending from the first end to the second end along a mid-line between the front surface and the back surface;
      a first portion defined by and between the front surface and the central longitudinal axis and a second portion defined by and between the back surface and the central longitudinal axis;
      a first series of recesses extending into the body portion from the front surface and terminating in the second portion of the body portion; and
      a second series of recesses extending into the body portion from the back surface and terminating in the first portion of the body portion;
   wherein each of the recesses in the first series are alternatingly arranged with each of the recesses in the second series along the central longitudinal axis from the first end to the second end of the body portion.

2. The spacer of claim 1, wherein the spacer comprises a height defined by the distance between the top surface and the bottom surface measured perpendicular to the central longitudinal axis, and a portion of each of the recesses in the first and second series has a depth greater than one-half the height of the spacer.

3. The spacer of claim 1, wherein each of the recesses in the first and second series defines a length extending along a direction between the front surface and the back surface, and a depth extending along a direction between the top surface and the bottom surface, the depth of the recess being variable along the length.

4. The spacer of claim 1, wherein at least two recesses have different dimensions.

5. The spacer of claim 1, wherein the recesses in the first and second series are substantially parallel.

6. The spacer of claim 1, wherein the recesses in the first and second series are approximately equally spaced along the longitudinal axis.

7. The spacer of claim 1 being made of a biocompatible material that is also a bioinert material.

8. The spacer of claim 7, wherein the biocompatible material is Ultra High Molecular Weight Polyethylene.

9. The spacer of claim 7, wherein the biocompatible material is capable of resisting tissue ingrowth and/or adhesion.

10. The spacer of claim 1, wherein the body portion is generally elliptical in cross-section transverse to the longitudinal axis.

11. The spacer of claim 1, wherein the first end and second end have different shapes from each other.

12. The spacer of claim 1, wherein the first end and second end each have a shape that substantially conforms to a contacted bone segment.

13. The spacer of claim 1, wherein at least a portion of the spacer is coated with at least one therapeutic agent.

14. The spacer of claim 13, wherein the therapeutic agent is an antibiotic.

15. The spacer of claim 13, wherein the therapeutic agent is an antiseptic.

16. The spacer of claim 13, wherein the at least one therapeutic agent is applied by spraying, dipping, soaking, impregnating, or chemical vapor deposition, or a combination thereof.

17. The spacer of claim 13, wherein the at least one therapeutic agent is selected at least in part from the group of IGF (insulin-like growth factors), TGF (transforming growth factors), FGB (fibroblast growth factors), EGF (epidermal growth factors), BMP (bone morphogenic proteins) and PDGF (platelet-derived growth factors).

18. The spacer of claim 1, wherein the body further comprises a bore defining a longitudinal axis, the bore being disposed in the body such that the longitudinal axis of the bore is coextensive with the longitudinal axis of the body.

19. The spacer of claim 18, wherein the spacer further comprises an outer surface, the bore having an inner surface that substantially conforms to the shape of the outer surface.

20. The spacer of claim 19, wherein the bore comprises about 90% of a cross sectional area of the body of the spacer.

21. The spacer of claim 18, wherein each end of the spacer has a cross-sectional dimension, wherein the bore has a diameter that is substantially smaller than the cross-sectional dimension of each end.

22. The spacer of claim 21, wherein there are a plurality of bores suitable for accepting at least one suture.

23. The spacer of claim 1, wherein the spacer has at least one bore, the bore having a longitudinal axis substantially non-parallel to that of the body portion, wherein there are a plurality of bores suitable for accepting at least one suture.

24. The spacer of claim 1, wherein the spacer is preformed in a preselected shape.

25. The spacer of claim 24, wherein the preselected shape is configured to substantially mimic at least a portion of removed bone.

26. The spacer of claim 25, wherein the removed bone is a portion of a human mandible.

27. The spacer of claim 26, wherein the removed bone is a portion of a human chin.

28. The spacer of claim 1, wherein at least a portion of the body portion has a dull finish to reduce glare in the surgical work site.

29. The spacer of claim 1, wherein at least a portion of the body portion has a roughened finish to reduce glare in the surgical work site.

30. The spacer of claim 1, wherein at least one of the ends has a roughened finish to enhance engagement of the end with the associated bone segment.

31. An orthopedic tissue spacer, comprising:
a body portion comprising:
a front side having a front surface, a back side having a back surface, a top having a top surface, a bottom having a bottom surface, the top and bottom surfaces extending between the front and back surfaces, the body portion further defining a first end and a second end opposite the first end, wherein the top surface and the bottom surface are separated by a distance therebetween which defines a height, the height being measured perpendicular to the central longitudinal axis;
a first series of recesses defined by the body portion and extending from the top surface in a direction toward the bottom surface, a plurality of the recesses in the first series terminating in the body portion at a location such that the plurality of the recesses in the first series extends through more than half the height of the body portion between the top surface and the bottom surface; and
a second series of recesses defined by the body portion and extending from the bottom surface in a direction toward the top surface, a plurality of the recesses in the second series terminating in the body portion at a location such that the plurality of the recesses in the second series extends through more than half the height of the body portion between the top surface and the bottom surface.

32. The tissue spacer of claim 31 wherein at least one of the first series of recesses and at least one of the second series of recesses alternate in position from the first end to the second end of the body portion.

33. The tissue spacer of claim 32, wherein the front surface and the back surface are separated by a distance therebetween, and at least one of the first series of recesses extends from the front surface toward the back surface a distance of at least one-half the distance between the front surface and the back surface.

34. The tissue space of claim 33 wherein at least one of the second series of recesses extends from the back surface toward the front surface a distance of at least one-half the distance between the front surface and the back surface.

35. The tissue spacer of claim 34 wherein the body portion is made of a biocompatible material that is also a bioinert material.

36. The tissue spacer of claim 34 wherein the body portion is made of ultra high molecular weight polyethylene.

37. The tissue spacer of claim 34 wherein the body portion further comprises a central, internal bore.

38. An orthopedic tissue spacer, comprising:
a body portion comprising:
a curved front side having a front surface, a curved back side having a back surface, a top having a top surface, a bottom having a bottom surface, the top and bottom surfaces extending between the front and back sides, the body portion further defining a first end and a second end opposite the first end, wherein the top surface and the bottom surface are separated by a distance therebetween which defines a height, the height being measured perpendicular to the central longitudinal axis;
a first series of recesses defined by the body portion and extending from the top surface in a direction toward the bottom surface, a plurality of the recesses in the first series extending through more than half the height of the body portion between the top surface and the bottom surface and terminating within the body portion; and a second series of recesses defined by the body portion and extending from the bottom surface in a direction toward the top surface, a plurality of the recesses in the second series extending through more than half the height of the body portion between the top surface and the bottom surface and terminating within the body portion.

39. The tissue spacer of claim 38 wherein at least one of the first series of recesses and at least one of the second series of recesses alternate in position from the first end to the second end of the body portion.

40. The tissue spacer of claim 39, wherein the front surface and the back surface are separated by a distance therebetween, and at least one of the first series of recesses extends from the front surface toward the back surface a distance of at least one-half the distance between the front surface to the back surface.

41. The tissue space of claim 40 wherein at least one of the second series of recesses extends from the back surface toward the front surface a distance of at least one-half the distance between the front surface and the back surface.

42. The tissue spacer of claim 41 wherein the body portion is made of a biocompatible material that is also a bioinert material.

43. The tissue spacer of claim 41 wherein the body portion is made of ultra high molecular weight polyethylene.

44. The tissue spacer of claim 41 wherein the body portion further comprises a central, internal bore.

* * * * *